United States Patent [19]

Amlong

[11] 4,008,716

[45] Feb. 22, 1977

[54] GAS DISPENSING ASSEMBLY

[75] Inventor: William R. Amlong, Miami, Fla.

[73] Assignee: Safety Laboratories, Inc., Miami, Fla.

[22] Filed: Jan. 9, 1975

[21] Appl. No.: 539,876

[52] U.S. Cl. .......................... 128/203; 128/142 R; 137/614.19; 251/337

[51] Int. Cl.² .......................... A61M 16/00

[58] Field of Search ............ 128/145.8, 145.5, 142, 128/142.2, 142.3, 146.4, 203, 274; 137/614.19; 267/70 R, 160 R, 1.5 R; 251/337

[56] References Cited

UNITED STATES PATENTS

| | | | |
|---|---|---|---|
| 1,551,908 | 9/1925 | Prouty | 128/142 |
| 2,854,001 | 9/1958 | Humblet | 128/142.2 |
| 2,877,766 | 3/1959 | Moore | 128/203 |
| 3,043,302 | 7/1962 | Spears et al. | 128/203 |
| 3,114,388 | 12/1963 | Hoen | 251/337 |
| 3,386,458 | 6/1968 | Wasserman et al. | 128/145.8 |

FOREIGN PATENTS OR APPLICATIONS

| | | | |
|---|---|---|---|
| 1,231,734 | 10/1960 | France | 128/203 |
| 800,210 | 8/1958 | United Kingdom | 128/203 |

*Primary Examiner*—Robert W. Michell
*Assistant Examiner*—Henry J. Recla
*Attorney, Agent, or Firm*—Ladas, Parry, Von Gehr, Goldsmith & Deschamps

[57] ABSTRACT

A gas dispensing assembly suitable for dispensing oxygen from a vessel pressurized to 1800 pounds per square inch, the assembly including a manually operable member to turn supply of oxygen from said vessel on and off, a regulator valve supplied with gas at the pressure inside of the vessel when the supply is turned on, a spring biased regulator operable to control the opening and closing of the regulator valve to regulate the pressure in an outlet to a desired pressure for supply of the gas to the interior of a face mask; the assembly being capable of supplying oxygen to the face mask for a period exceeding 15 minutes at a flow rate exceeding 6 liters per minute with little variation of that flow rate with variation of pressure of the supply of oxygen.

10 Claims, 4 Drawing Figures

GAS DISPENSING ASSEMBLY

This invention relates to a gas dispensing assembly and particularly, though not exclusively to a dispenser for dispensing oxygen when desired from a storage vessel to a face mask.

A typical example of prior art oxygen supplying assembly is shown in U.S. Pat. No. 3,186,407 (a similar disclosure is found in Canadian Patent No. 751,725). This prior art device meters oxygen from a vessel through an orifice and supplies this oxygen to a face mask by way of a demand valve. The rate of supply of oxygen to the face mask varies substantially with changes in the supply pressure and under any circumstances insufficient oxygen will be supplied to a user in the absence of adequate inhalation by the user. The operational characteristics of the earlier device are not satisfactory and do not meet the requirements of today for the operation of such devices.

Attention is also drawn to U.S. Pat. Nos. 3,547,143, 2,674,829, 2,906,288, 2,819,728, 3,482,591, 2,119,473, 3,538,930, 3,386,458, 3,587,642 and 2,565,560 all of which relate to various aspects of regulators.

It is an object of the present invention to provide a gas dispensing assembly capable of dispensing, when desired, at least six liters per minute of oxygen from a pressurized storage vessel of oxygen with little change in supply rate with changes in the pressure of the oxygen supply as the vessel is emptied.

It is also an object of the present invention to provide such a dispensing assembly with a conveniently operated arrangement for opening the high pressure control valve of the cylinder when a supply of oxygen is desired and to provide a technical and operational advance over the prior art devices such as that disclosed in U.S. Pat. No. 3,186,407 and the other United States Patents made of record above.

According to one aspect of the invention a self-contained oxygen dispensing assembly comprising a housing defining an inlet passage, adapted for connection to a source of oxygen at a high pressure, and an outlet passage, a supply control means in said housing to control oxygen flow from said source to said inlet passage, an inlet regulator valve disposed in said inlet passage to control gas flow from said source through said inlet passage, a resiliently biased regulator disposed in said housing and together with said housing defining a pressure regulation chamber with which, by way of said inlet regulator valve said inlet passage communicates, said regulator being arranged to control said inlet regulator valve to control flow of high pressure gas from said inlet passage to regulate pressure in said chamber to a desired pressure, said outlet passage extending from said chamber and a face mask connected to said outlet passage.

According to a preferred aspect the assembly further comprises a high pressure oxygen supply vessel connected to said housing to supply oxygen to said inlet passage, said vessel having an outlet demand valve and said supply control means being operable to open said outlet demand valve and said supply control means comprises a member rotatably mounted in a sealed manner through said inlet passage in said housing, said housing is comprised of a connector part connected to said vessel and a regulator housing part arranged for rotation in screw threads relative to said connector part, said member being movable with and by rotation of said regulator housing part relative to said connector part between a position in which said member cooperated with said outlet demand valve to open said outlet demand valve and a position in which said member permits said outlet demand valve to close.

The invention will now be described, by way of example, with reference to the accompanying drawings, in which.

Figure 1:
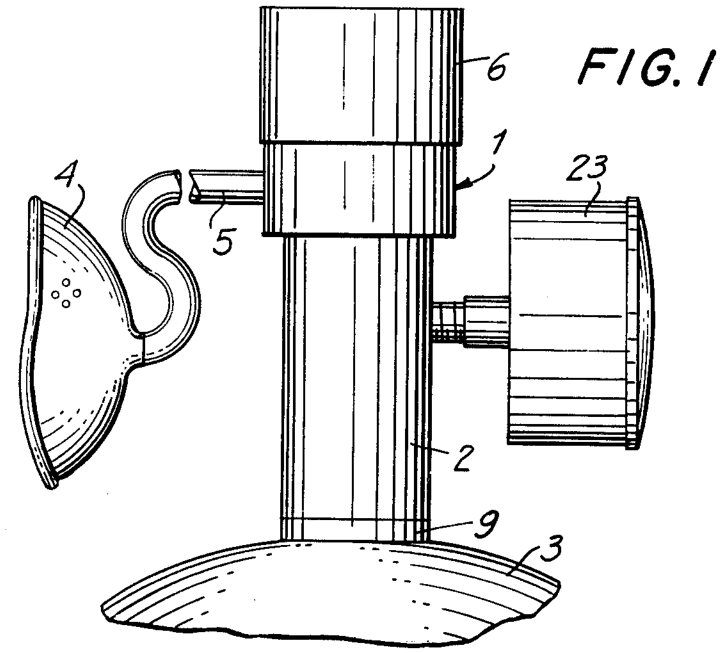
FIG. 1 is a side elevation of an oxygen dispensing assembly with attached face mask and tubing and with a decorative cap in place.
Figure 2:
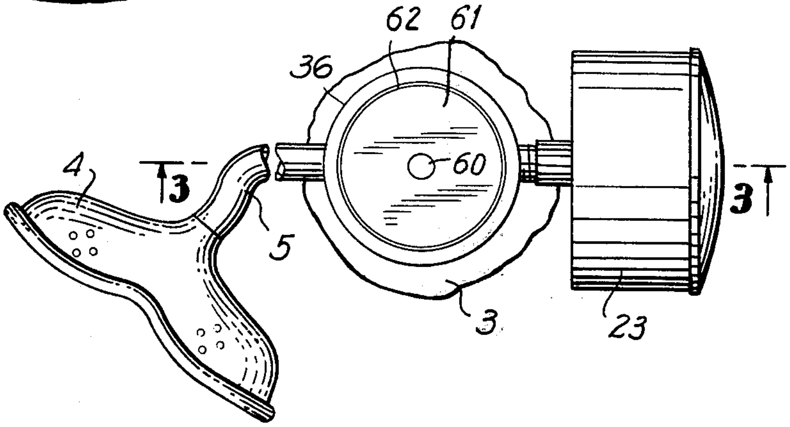
FIG. 2 is a plan view of the assembly shown in FIG. 1 with the decorative cap omitted.
Figure 4:
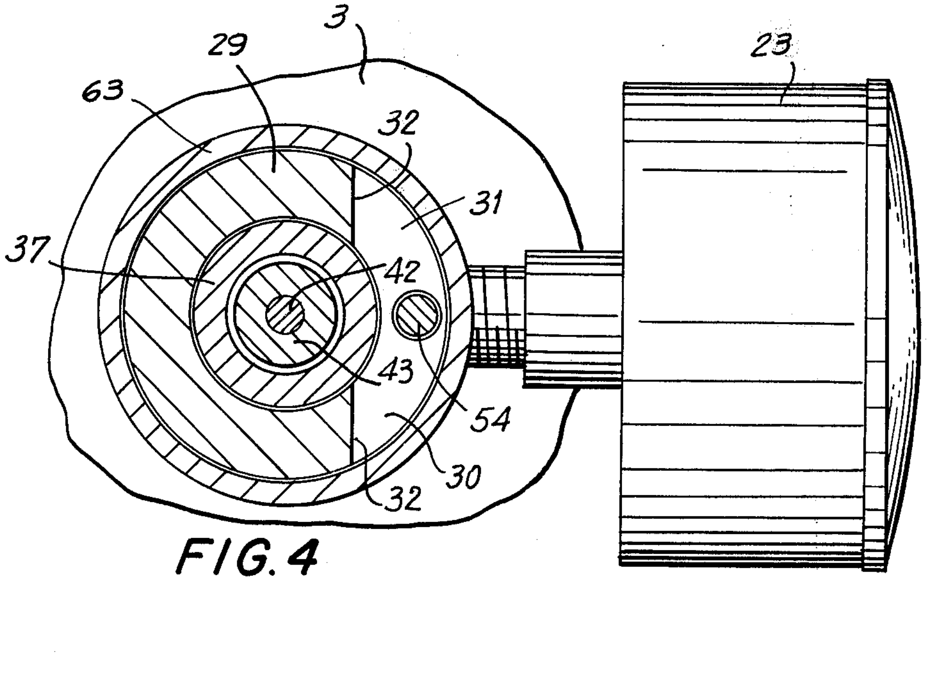
FIG. 4 is a sectional plan view taken along section lines 4—4 of FIG. 3.
Figure 3:
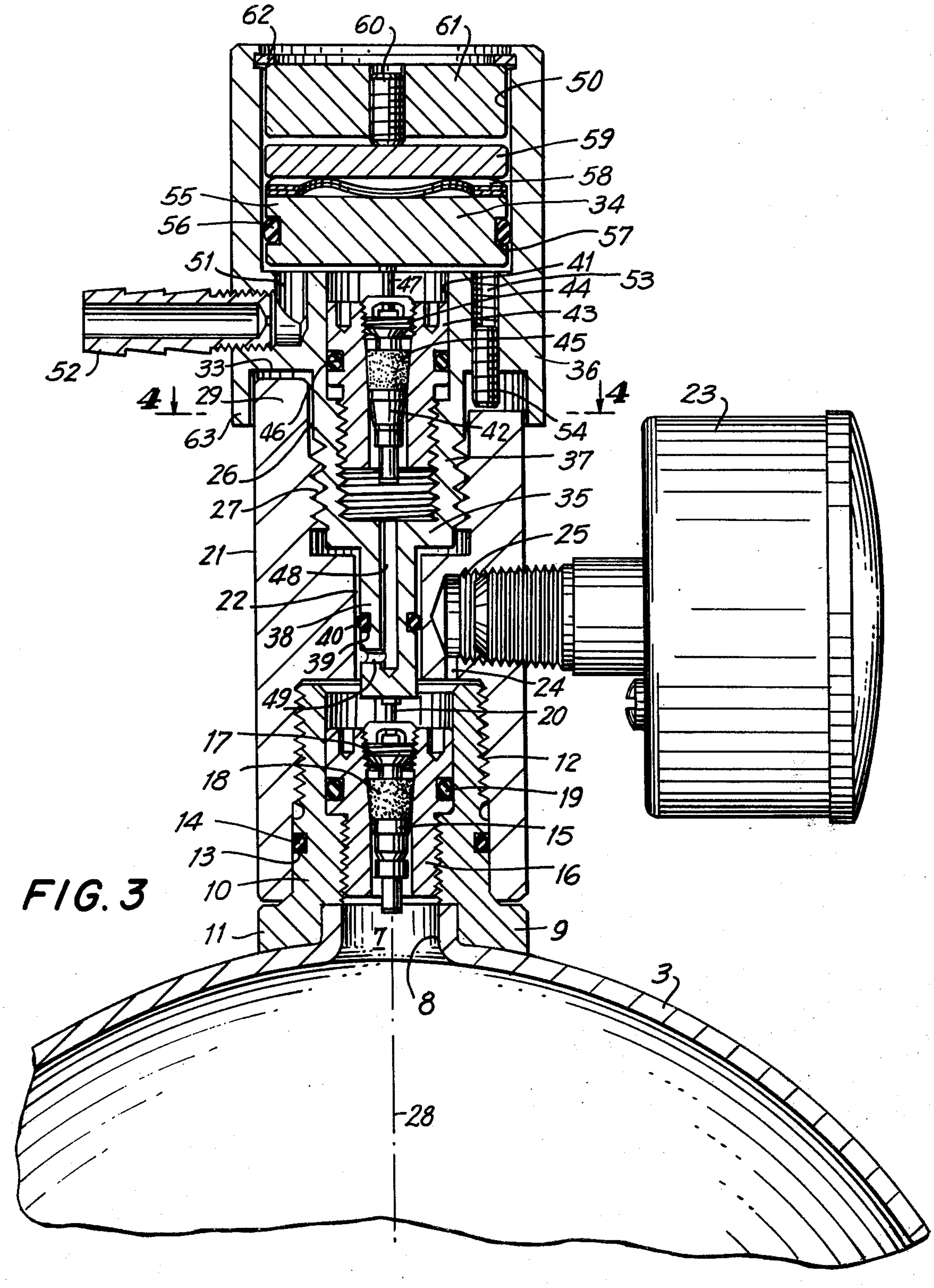
FIG. 3 is a sectional elevation of the assembly shown in FIG. 1 taken along section lines 3—3 of FIG. 2 and with the face mask, supply tubing and decorative cap omitted.

In the drawings an oxygen dispensing assembly includes a regulating and outlet control arrangement 1, a connector and pressure gauge assembly 2 and a gas storage vessel 3. As shown in FIGS. 1 and 2 a face mask 4 is connected by a flexible tube 5 to the control arrangement 1 and as shown in FIG. 1 the upper portion of the control arrangement 1 is covered by a decorative cap 6.

In this preferred example, the oxygen storage vessel is a hollow steel sphere of a size which will contain approximately 130 liters of available oxygen when filled to 1,800 pounds per square inch. The sphere is constructed from two overlapping hemispherical pressings copper brazed together, one of the pressings being formed with a central opening 7 defined by a collar 8, integrally formed with that hemisphere, to which and the surrounding portion of that hemisphere a vessel outlet valve assembly 9 is copper brazed.

The vessel outlet valve assembly 9 includes a tubular member 10 having a flange 11, to which the spherical vessel is copper brazed at one end and a threaded periphery 12 adjacent the other end. Between the threaded periphery and the flange is an external annular groove 13 which houses an O-ring seal 14. Housed within the tubular member 10 and also forming part of the vessel outlet valve assembly 9 is a demand valve 15 and a demand valve support 16. The demand valve 15 is of a type well known in the art and variously known as a "Dill" or "Schrader" valve. This demand valve 15 has a threaded portion 17 by means of which it is mounted in a cooperating screw thread of the demand valve support 16. The demand valve 15 is sealed to the demand valve support by an annular frusto-conical resilient seal 18 and is held normally closed by a spring (not shown) and gas pressure inside the vessel 3.

The demand valve support 16 is attached to the tubular member 10 by screw threads and leakage of gas between the tubular member and the demand valve support is prevented by an O-ring 19 housed in an annular external groove in the demand valve support and cooperating with both the demand valve support and the tubular member.

The demand valve 12 is opened only by an axial force applied to an operating stem 20 in a direction toward the vessel 3 sufficient to overcome the valve closing force resulting from the combined action of the spring mentioned above and the gas pressure in the vessel.

The connector and pressure gauge assembly 2, attached by screw threads to threads 12 of the vessel 3 and sealed thereto by O-ring 14, comprises an elongate substantially cylindrical member 21 having a central passage 22 of circular cross-section extending longitudinally therethrough and a pressure gauge 23 connected to the elongate cylindrical member 21 by screw threads and communicating with the outlet of demand valve 15 by way of passage 24 to provide an indication of gas pressure at the inlet to the passage 22. The passage 22 provides communication from the vessel 3 by way of demand valve 15 to the regulating and outlet control arrangement 1.

A radial passage 25, extending from the passage 24 and having screw threads therein, provides for the mounting of the pressure gauge 23 and the communication of that pressure gauge with the passage 24.

The end of passage 22 remote from the vessel 3 when the connector and pressure gauge assembly 2 is connected to the pressure vessel opens into a counter bore 26 having a thread 27 formed on the interior wall thereof. When the connector and pressure gauges 72 is attached to the vessel 3 the demand valve 15, threaded periphery 12, passage 22 and counter bore 26 are all coaxially disposed about a longitudinal axis 28 of the dispensing assembly.

The annular end 29 of the cylindrical member 21 which surrounds the open end of the counter bore 26 has a cut away section 30 defined by an end surface 31 of semi-circular form and faces 32 extending from the end surface 31 parallel with the axis 28 to the end face 33 of the annular end 29.

The regulating and outlet control arrangment 1 includes a spring biased regulator 34 and an arrangement 35 for opening the demand valve 15 of the vessel 3 when a flow of oxygen is desired. The regulating and outlet control arrangement includes a housing 36 of generally elongate cylindrical form with a threaded projection 37 extending axially from one end into engagement with the threads of counter bore 26. Extending axially from the free end of the projection 37 is a demand valve operating projection 38 of slightly smaller diameter than the diameter of passage 22. The projection 38 has an annular groove 39 in which is housed an 0-ring seal 40. The O-ring seal 40 cooperates with the groove 39 and the wall of passage 22 to prevent flow of gas therebetween.

Projection 38 extends through passage 22 into contact with the operating stem 20 of demand valve 15 whereby relative rotation of the housing 36 and cylindrical member 21 will, by virtue of engagement of the threads of projection 37 and counterbore 26, depress or release the operating stem 20 to open or allow to close the demand valve 15.

The end of housing 36 remote from projection 38 defines a cylindrical chamber which houses the regulator 34 and centrally from the inner end of which extends a valve housing bore 41 similar to the tubular bore of the tubular member 10. Housed within the bore 41 is a regulator valve 42 and a regulator valve support 43. The regulator valve 42 is of a type well known in the art and variously known as "Dill" or "Schrader" valve. This valve is similar to the valve 15. The regulator valve 42 has a threaded portion 44 by means of which it is mounted in a cooperating screw thread of the regulator valve support 43. The regulator valve 42 is sealed to the regulator valve support by an annular frusto-conical resilient seal 45 and is held normally closed by a spring (not shown) and gas pressure when gas flows from vessel 3.

The regulator valve support 43 is attached to the valve housing bore 41 by screw threads and leakage of gas between the tubular member and the regulator valve support is prevented by an O-ring seal 46 housed in an annular external groove in the regulator valve support and cooperating with both the regulator valve support and the valve housing bore.

The regulator valve 42 is opened only by an axial force applied to an operating stem 47 in a direction toward the vessel 3 sufficient to overcome the valve closing force resulting from the combined action of the spring mentioned above and gas pressure when released from the vessel 3.

From the vessel side of the regulator valve 42 axially through the projection 38 extends a blind bore 48. A radial bore 49 extends from the periphery of projection 38 on the demand valve 15 side of O-ring 40, to passage 48. When demand valve 15 is open gas, from vessel 3 passes between the wall of passage 22 and projection 38 through passages 49 and 48 to regulator valve 42. When the demand valve is open gas from vessel 3 also passes by way of passage 24 to pressure gauge 23 thereby to provide an indication of gas pressure in vessel 3.

The cylindrical chamber 50 which houses regulator 34 is connected at its lower end to the outlet of regulator valve 42 and by a passage 51 to an outlet nipple 52 arranged for connection of tube 5 thereto. Also extending from the inner end of the cylindrical chamber 50 is threaded bore 53 in which is housed a threaded stop 54. The threaded bore 53 is arranged so that the threaded stop 54 can extend into the cut away section 30 of cylindrical member 21 to control the extent of relative rotation of the housing 36 and the cylindrical member 21. The extend of this relative rotation is controlled by the positioning of the faces 32 respectively with which the stop 54 will abut at opposite ends of the permitted relative rotation. This relative rotation is arranged such that projection 38 will hold demand valve 15 open at one end of the rotation and will allow demand valve 15 to close at the other end of relative rotation.

Regulator 34 comprises a piston 55 dimensioned for sliding axial movement in the cylindrical chamber 50 and arranged to contact the operating stem 47 of regulator valve 42. An 0-ring seal 56 is housed in an annular groove 57 extending around the periphery of the piston 55 in cooperation with both the piston 55 and the cylindrical wall of cylindrical chamber 50.

On the side of piston 55 remote from regulator valve 42 is a spring 58 comprised of two superimposed wave spring washers. The longitudinal axis of spring 58, piston 55 and regulator valve 42 is coincident with the longitudinal axis 28 of the connector and pressure gauge assembly and the line of action is along that axis. The spring 58 is backed by an adjusting disc 59. The spring 58 and disc 59 are radially located by the cylindrical chamber and the spring tension is controlled by an adjusting screw 60 mounted in a cylindrical member 61 and extending along the longitudinal axis 28 of the connector and pressure gauge assembly into engagement with the center of adjusting disc 59. The cylindrical member 61 is retained in the cylindrical chamber by a spring retaining clip 62 housed in a groove in the cylindrical chamber adjacent the open end thereof. A decorative cap is used to cover the open end of the cylindrical chamber 50. The housing 36 is provided with an annular skirt 63 which, when threaded projection 37 is in engagement with the threads of counterbore 26 extends around the annular end 29 of the cylindrical member 21 to cover the cut away section 30.

In operation, when the oxygen dispensing assembly is screwed onto vessel 3 and housing 36 is turned, the projection 38 depresses stem 20 to open demand valve 15, thereby allowing oxygen from the vessel 3 to pass to the pressure gauge 23 and between the projection 38 and passage 22 through passages 49 and 48 to the regulator valve 42. The pressure differential across the regulator valve 42 together with the spring pressure applied by the biasing spring of regulator valve 42 oppose the spring force applied by spring 58 to the piston 55. The arrangement is such that when the pressure valve 3 is from 20 to 1,800 pounds per square inch above ambient pressure, the piston will control opening of the regulator valve 42 to maintain an oxygen flow through outlet passage 51 of approximately six liters per minute.

When an oxygen supply is not required the housing 36 is turned relative to cylindrical member 21 to move projection 38 away from stem 20 sufficiently to permit demand valve 15 to close.

I claim:

1. A self-contained oxygen dispensing assembly for use in combination with an interchangeable high pressure oxygen supply vessel having an outlet demand valve comprising: a housing defining an inlet passage, having first and second ends and an outlet passage, said first end of said inlet passage having screw means suitable for attachment of said inlet passage to a said interchangeable high pressure oxygen supply vessel for the supply of oxygen to said inlet passage, said vessel having an outlet demand valve; a supply control means operable to open said outlet demand valve, when said first end of said inlet passage is connected to said vessel, to control oxygen flow from said vessel to said inlet passage; an inlet regulator valve disposed in said inlet passage adjacent said second end to control gas flow from said vessel through said inlet passage; a resiliently biased regulator disposed in said housing at said second end of said inlet passage and including a pressure regulator chamber, said second end of said inlet passage terminating in said pressure regulation chamber, said regulator including means for providing cooperation between said inlet regulator valve and said spring biased regulator for controlling flow of high pressure oxygen from said inlet passage whereby the pressure in said chamber is regulated to a desired pressure, said outlet passage extending from said chamber; and a face mask connected to said outlet passage; wherein said supply control means comprises a member supported in and extending in a sealed manner through said inlet passage to said first end for movement, relative to said first end thereof, to open said outlet demand valve, and said housing is comprised of a connector part which defines said first end of said inlet passage, a regulator housing part connected to said connector part for rotation relative thereto, said regulator housing part cooperating with said member to move said member in response to said relative rotation, said relative rotation being between a position in which said member cooperates with said outlet demand valve to open said outlet demand valve and a position in which said member permits said outlet demand valve to close, and means to restrict said relative rotation to rotation between said positions.

2. An assembly according to claim 1, in which said member is a cylindrical projection integrally formed with said regulator housing part and said regulator housing part is connected to said connector part by screw means whereby said relative rotation moves said projection longitudinally of its cylindrical axis to operate said outlet demand valve.

3. An assembly according to claim 1, comprising a high pressure oxygen supply vessel connected to said housing in communication with said inlet passage to supply oxygen thereto, said vessel having an outlet demand valve which cooperates with said supply control means and is opened thereby to allow oxygen to flow from the vessel to the inlet passage.

4. An oxygen dispensing assembly according to claim 3, wherein said vessel is a spherical tank including an outlet assembly having screw means cooperating with the inlet passage screw means and an outlet to provide communication from said vessel to said inlet passage, said outlet demand valve being disposed in said outlet to control flow therethrough, said outlet assembly including an annular O-ring seal to seal said housing to said outlet assembly.

5. An oxygen dispensing assembly according to claim 3, wherein said vessel is a spherical tank comprising two substantially hemispherical steel members copper brazed together with one of the steel members defining an opening communicating with an outlet assembly which is copper brazed to said one steel member.

6. An oxygen dispensing arrangement according to claim 3, wherein said vessel is a spherical tank, which when full is pressurized to 1800 pounds per square inch, having an oxygen capacity of 130 liters at 1800 pounds per square inch, said gas dispensing assembly is adapted to dispense said oxygen on demand at at least about 6 liters per minute for a total dispensing time exceeding 15 minutes.

7. An oxygen dispensing arrangement according to claim 6, wherein said regulator is adapted to maintain a pressure of oxygen in said chamber in a range from about 12 pounds per square inch above ambient pressure to about 16 pounds per square inch above ambient pressure with a variation of pressure in said inlet passage in a range from about 20 pounds per square inch above ambient pressure to about 1800 pounds per square inch above ambient pressure and said outlet passage is arranged to pass oxygen at a rate in a range from about 6 liters per minute to about 8 liters per minute with said range of pressure in said chamber.

8. An assembly according to claim 1, wherein said regulator comprises a circular piston the periphery of which houses a seal in sealing engagement with said housing, a wave spring washer means housed in said housing on the side of said piston remote from said chamber and acting between said housing and said piston to oppose force applied to said piston by pressure of gas in said chamber and to bias said piston in a direction which will open said inlet regulator valve when the gas pressure in said chamber is below said desired pressure.

9. An oxygen dispensing assembly according to claim 1, wherein said face mask has vents to allow escape of oxygen when the outlet demand valve is open and the inhalation rate of a user is exceeded by the rate of oxygen supply from said gas dispensing assembly.

10. An assembly according to claim 1, wherein said housing comprises a brass connector part defining said inlet passage, adapted for connection to a source of high pressure gas and a brass regulator housing part housing said inlet regulator valve and said regulator, said regulator including a piston diaphragm which with said regulator valve defines said chamber from which said outlet passage extends.

* * * * *